United States Patent
Baba et al.

(10) Patent No.: US 11,471,633 B2
(45) Date of Patent: Oct. 18, 2022

(54) MASK

(71) Applicant: NIHON KOHDEN CORPORATION, Tokyo (JP)

(72) Inventors: Yuya Baba, Tokorozawa (JP); Isao Matsubara, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 431 days.

(21) Appl. No.: 16/564,487

(22) Filed: Sep. 9, 2019

(65) Prior Publication Data

US 2020/0101248 A1   Apr. 2, 2020

(30) Foreign Application Priority Data

Sep. 27, 2018  (JP) .............................. JP2018-181852

(51) Int. Cl.
*A61M 16/06*   (2006.01)

(52) U.S. Cl.
CPC .... *A61M 16/0611* (2014.02); *A61M 16/0683* (2013.01); *A61M 2205/0238* (2013.01)

(58) Field of Classification Search
CPC ............ A61M 16/06–0694; A61M 2016/0661
See application file for complete search history.

(56) References Cited

U.S. PATENT DOCUMENTS

| | | | |
|---|---|---|---|
| 6,412,487 B1 * | 7/2002 | Gunaratnam | A61M 16/06 128/205.25 |
| 7,640,933 B1 * | 1/2010 | Ho | A61M 16/0666 128/206.24 |
| 2008/0032119 A1 * | 2/2008 | Feldhahn | A61M 16/0858 428/332 |
| 2009/0139525 A1 * | 6/2009 | Schirm | A61M 16/0605 128/205.25 |
| 2012/0204881 A1 * | 8/2012 | Davidson | A61M 16/0683 128/206.25 |
| 2018/0169366 A1 * | 6/2018 | Bell | A61M 16/06 |
| 2019/0001093 A1 * | 1/2019 | Rutan | A61M 16/0616 |

FOREIGN PATENT DOCUMENTS

JP     2005-211208 A     8/2005

* cited by examiner

*Primary Examiner* — Valerie L Woodward
(74) *Attorney, Agent, or Firm* — Pearne & Gordon LLP

(57) ABSTRACT

A mask includes: a mask body configured to define a space that covers at least one of a nose and a mouth of a subject; and a cushion member extending along a peripheral edge portion of the mask body. The cushion member includes: a first region that includes a portion that contacts a face of the subject when fitted; and a second region positioned between the first region and the mask body. A surface of the first region has a higher non-adhesive property than a surface of the second region, and the second region has transparency that allows the space to be seen through.

9 Claims, 4 Drawing Sheets

[FIG. 1]
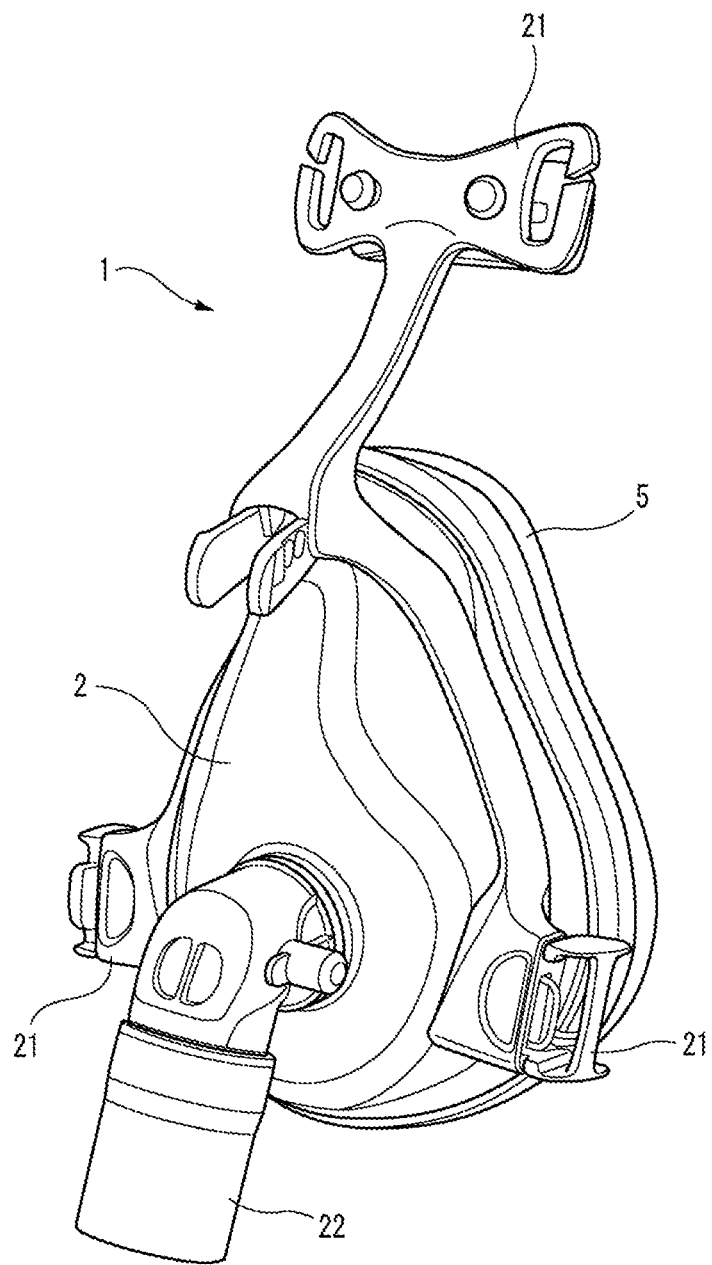

[FIG. 2]
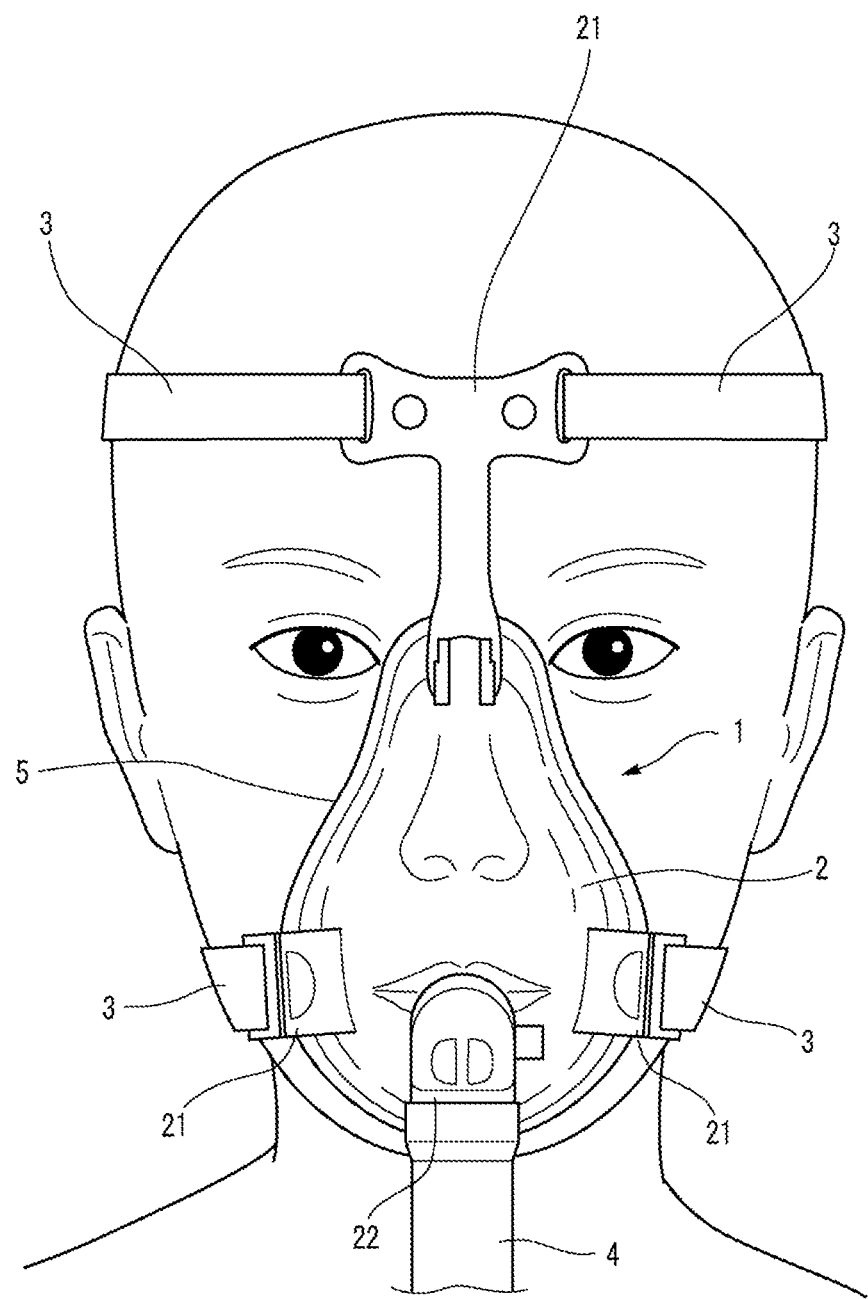

[FIG. 3]
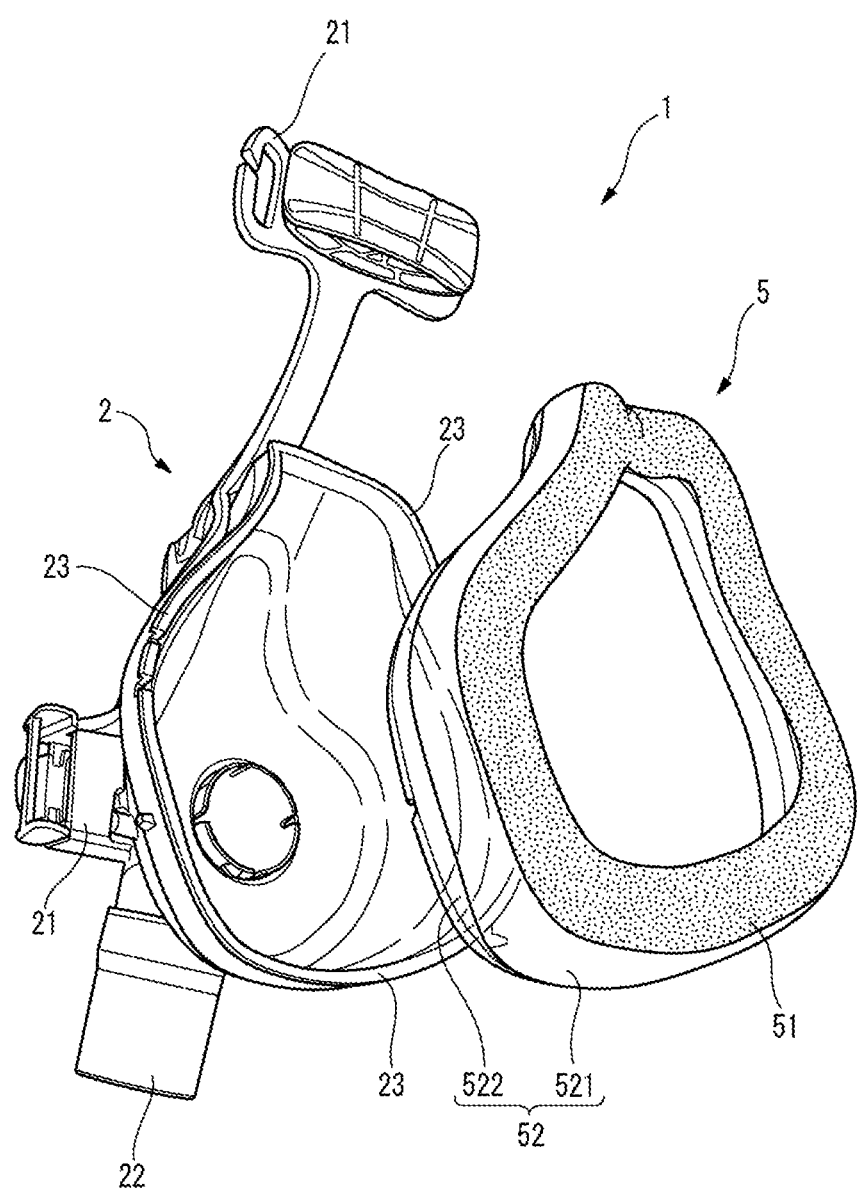

[FIG. 4]
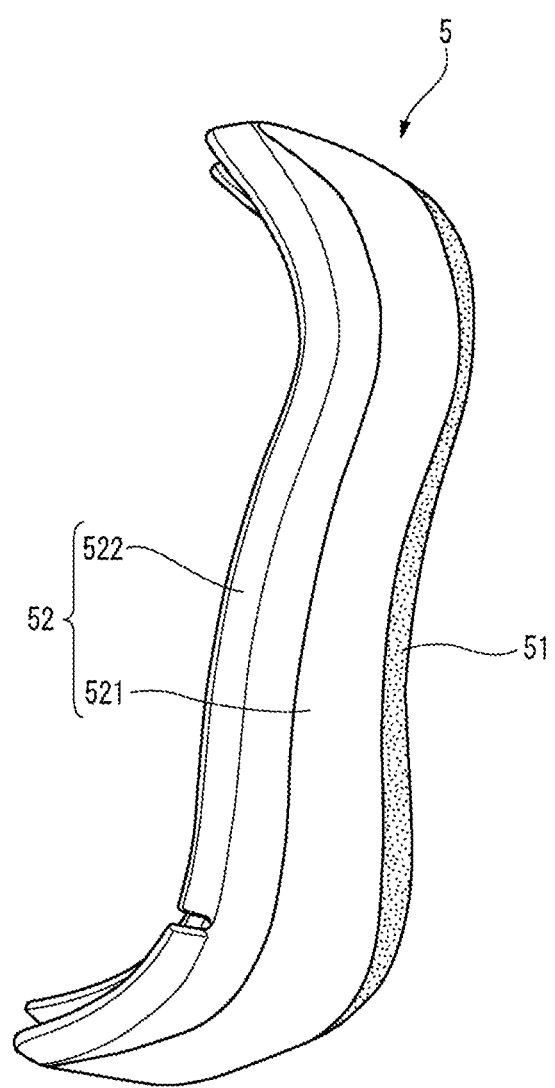

MASK

CROSS-REFERENCE TO RELATED APPLICATIONS

This application is based on and claims priority under 35 USC 119 from Japanese Patent Application No. 2018-181852 filed on Sep. 27, 2018, the contents of which are incorporated herein by reference.

TECHNICAL FIELD

The presently disclosed subject matter relates to a medical mask fitted to a face of a subject or a patient to support a respirator, for example.

BACKGROUND

JP-A-2005-211208 discloses this kind of mask. The mask includes a central member and a base member. The central member defines a space that covers a nose and a mouth of a subject. The base member extends along a peripheral edge portion of the central member. The base member is formed to have elastic flexibility which allows the base member to be fitted along curvature of a face of the subject and to contact the face.

The base member of the mask described in JP-A-2005-211208 prevents air leakage by providing high adhesion with respect to the face of the subject. However, such high adhesion tends to cause discomfort to the subject especially when the mask is fitted for a long time.

An object of the presently disclosed subject matter is to suppress the discomfort given to the subject when the mask is fitted.

SUMMARY

A mask relating to an aspect for achieving the object described above includes: a mask body configured to define a space that covers at least one of a nose and a mouth of a subject; and a cushion member extending along a peripheral edge portion of the mask body. The cushion member includes: a first region that includes a portion that contacts a face of the subject when fitted; and a second region positioned between the first region and the mask body. A surface of the first region has a higher non-adhesive property than a surface of the second region, and the second region has transparency that allows the space to be seen through.

BRIEF DESCRIPTION OF DRAWINGS

FIG. 1 illustrates an appearance of a mask according to an embodiment;

FIG. 2 illustrates an example of using the mask of FIG. 1;

FIG. 3 illustrates a mask body and a cushion member constituting the mask of FIG. 1; and FIG. 4 illustrates an appearance of the cushion member of FIG. 3 in a side view.

DESCRIPTION OF EMBODIMENTS

An example of an embodiment will be described in detail with reference to the drawings. FIG. 1 illustrates an appearance of a mask 1 according to the embodiment. As illustrated in FIG. 2, the mask 1 is fitted to a face of a subject. The mask 1 is used, for example, to support a respirator.

The mask 1 can include a mask body 2. The mask body 2 defines a space covering a nose and a mouth of the subject. The mask body 2 is formed of a material having transparency that allows the space to be seen through. Polycarbonate may be exemplified as such a material. Therefore, as illustrated in FIG. 2, when the subject wearing the mask 1 is viewed from front, the nose and the mouth of the subject can be visually checked through the mask body 2.

As illustrated in FIG. 1, the mask body 2 can include a plurality of belt attaching portions 21. As illustrated in FIG. 2, a belt may be attached to the respective belt attaching portions 21. Each belt 3 is used to fix the mask 1 to a head of the subject.

As illustrated in FIG. 1, the mask body 2 can include a hose connecting portion 22. The hose connecting portion 22 establishes communication between inside and outside of the mask body 2. As illustrated in FIG. 2, a hose 4 for supplying and discharging air is connected to the hose connecting portion 22.

The mask 1 can include a cushion member 5. As illustrated in FIG. 3, the cushion member 5 extends along a peripheral edge portion 23 of the mask body 2. A state illustrated in FIGS. 1 and 2 is obtained when the cushion member 5 is attached to the peripheral edge portion 23 of the mask body 2.

The cushion member 5 is flexible enough to be deformed along a shape of the face of the subject. Flexibility of the cushion member 5 is higher than flexibility of the mask body 2. In other words, the mask body 2 has higher rigidity than the cushion member 5.

As illustrated in FIGS. 3 and 4, the cushion member 5 can include a first region 51 and a second region 52. The second region 52 further includes a side wall portion 521 and a fitting portion 522. The first region 51 includes a portion which contacts the face of the subject. The fitting portion 522 is a portion which is fitted to the peripheral edge portion 23 of the mask body 2. The side wall portion 521 is a portion defined between the first region 51 and the fitting portion 522. The side wall portion 521 is a portion that separates the inside and the outside of the mask 1 at a position closer to the face of the subject than the mask body 2.

A surface of the first region 51 has a higher non-adhesive property than a surface of the second region 52. Meanwhile, the second region 52 has higher transparency than the first region 51. That is, the cushion member 5 can include the first region 51 and the second region 52 whose non-adhesive properties and transparency are different.

According to such configuration, since the first region 51, which includes the portion that contacts the face of the subject, has a relatively high non-adhesive property, discomfort given to the subject when the mask 1 is fitted can be suppressed. In addition, since the second region 52, which is a portion of the cushion member 5 extending along the peripheral edge portion 23 of the mask body 2, has relatively high transparency, the inside of the mask 1 can be visually checked through the side wall portion 521, which is closer to the face of the subject than the mask body 2, for example, even from a lateral side. Accordingly, it is possible to help a medial worker to visually check, and to suppress the discomfort of the subject while wearing the mask 1.

Specifically, the surface of the first region 51 is processed to form an uneven surface. The term "uneven" used in this specification means that the surface has concave and convex portions having sizes that do not affect a contour shape of the cushion member 5 as illustrated in FIG. 3. The concave and convex portions are distinguished from concave and convex portions with larger scales formed by the curved contour illustrated in FIG. 3. Examples of processing for forming the uneven surface include: forming of grooves and patterns, wrinkling, embossing, and the like.

According to such configuration, a contact area between the surface of the first region 51 and a surface of the face of the subject is reduced, and a non-adhesive property higher than that of the surface of the second region 52 is realized. Accordingly, it is possible to enhance an effect of suppressing the discomfort of the subject caused by the wearing of the mask 1.

In particular, in a case where wrinkling or embossing is applied to the first region 51, it is possible to realize a point contact between the surface of the first region 51 and the face of the subject. Accordingly, the effect of suppressing the discomfort of the subject can be further enhanced. In addition, the surface of the first region 51, which has the higher non-adhesive property than the surface of the second region 52, can be easily formed using a relatively inexpensive molding technique. As a result, although the transparency of the first region 51 is reduced, since the second region 52, which has higher transparency than the first region 51, is positioned between the first region 51 and the mask body 2, visibility of the inside of the mask 1 can be secured for the medical worker.

In the present embodiment, the first region 51 and the second region 52 are an integrally molded product made of silicon or vinyl chloride.

According to such configuration, workability for assembling the mask 1 is improved, and a boundary position can be accurately determined between the first region 51 and the second region 52. In particular, in a case where the relatively high non-adhesive property of the first region 51 is obtained by transferring wrinkles or embossed effect on an inner surface of a molding die, the effect of reducing a manufacturing cost is enhanced.

The embodiment described above is intended to facilitate understanding of the presently disclosed subject matter, and is not intended to limit the presently disclosed subject matter. The presently disclosed subject matter may be modified and improved without departing from the spirit of the presently disclosed subject matter.

The non-adhesive property of the first region 51 can be realized by means other than the processing of forming the uneven surface. For example, the non-adhesive property higher than that of the surface of the second region 52 can be realized by applying a fluorine coating to a portion corresponding to the first region 51 on a surface of the cushion member 5. In this case, since both the first region 51 and the second region 52 have transparency that allows the space defined by the mask body 2 to be seen through, the visibility of the inside of the mask 1 is further improved for the medical worker. The fluorine coating and the processing of forming the uneven surface may also be combined.

Alternatively, the non-adhesive property higher than that of the surface of the second region 52 may also be realized by adhering a sheet made of a fiber material to the portion corresponding to the first region 51 on the surface of the cushion member 5.

In the embodiment described above, the mask body 2 covers the nose and the mouth of the subject. However, the mask body 2 may be configured to cover any one of the nose and the mouth of the subject depending on application of the mask.

A mask relating to an aspect for achieving the object described above includes: a mask body configured to define a space that covers at least one of a nose and a mouth of a subject; and a cushion member extending along a peripheral edge portion of the mask body. The cushion member includes: a first region that includes a portion that contacts a face of the subject when fitted; and a second region positioned between the first region and the mask body. A surface of the first region has a higher non-adhesive property than a surface of the second region, and the second region has transparency that allows the space to be seen through.

According to the configuration described above, the mask which includes the cushion member is provided, and the cushion member including the first region and the second region whose non-adhesive properties are different. Since the first region, which includes the portion that contacts the face of the subject, has a relatively high non-adhesive property, it is possible to suppress discomfort given to the subject when the mask is fitted.

In addition, since the second region, which is a portion of the cushion member extending along the peripheral edge portion of the mask body, has the transparency that allows inside of the mask to be seen through, the inside of the mask can be visually checked through a portion closer to the face of the subject than the mask body, for example, even from a lateral side. Accordingly, it is possible to support a medial worker's visual check, and to suppress the discomfort of the subject while wearing the mask.

What is claimed is:

1. A mask, comprising:
   a mask body configured to define a space that covers at least one of a nose and a mouth of a subject; and
   a cushion member extending along a peripheral edge portion of the mask body, the cushion member including:
      a first region that includes a portion that is configured to contact a face of the subject when fitted; and
      a second region positioned between the first region and the mask body, wherein the first region of the cushion member has an uneven surface that is wrinkled so that the first region has a higher non-adhesive property than a surface of the second region, and
   the second region has transparency that allows the space to be seen through the second region.

2. The mask according to claim 1, wherein the portion of the first region is configured to be in a point contact with the face of the subject when fitted.

3. The mask according to claim 1, wherein the uneven surface of the first region is coated with fluorine.

4. The mask according to claim 1, wherein the first region and the second region are an integrally molded product made of silicon or vinyl chloride.

5. The mask according to claim 1, wherein the second region comprises:
   a side wall portion that separates an inside and an outside of the mask at a position configured to be closer to the face of the subject than the mask body; and
   a fitting portion that is fitted to the peripheral edge portion of the mask body.

6. The mask according to claim 1, wherein the mask body has higher rigidity than the cushion member.

7. The mask according to claim 1, further comprising a plurality of belt attaching portions to each of which a belt is attached.

8. The mask according to claim 1, wherein a sheet made of a fiber material is adhered to the uneven surface of the first region.

9. The mask according to claim 1, wherein the mask body has transparency that allows the space to be seen through the mask body.

* * * * *